United States Patent [19]

Morita et al.

[11] Patent Number: 4,656,250

[45] Date of Patent: Apr. 7, 1987

[54] [NLE⁸, NLE¹⁸, TYR³⁴ OR PHE³⁴]-H-PTH PEPTIDE DERIVATIVES

[75] Inventors: Kaoru Morita; Shigeo Katsuragi; Toshiharu Noda, all of Shizuoka, Japan

[73] Assignee: Toyo Jozo Kabushiki Kaisha, Shizuoka, Japan

[21] Appl. No.: 637,735

[22] Filed: Aug. 6, 1984

[30] Foreign Application Priority Data

Aug. 5, 1983 [JP] Japan .................. 58-144016
Jul. 13, 1984 [JP] Japan .................. 59-144114

[51] Int. Cl.⁴ ............. C07K 7/10; A61K 43/00; G01N 33/534
[52] U.S. Cl. ................. 530/324; 424/1.1; 436/545
[58] Field of Search ............ 260/112.5 R; 424/1.1; 436/545; 530/324

[56] References Cited

U.S. PATENT DOCUMENTS 3,886,132 5/1975 Brewer et al. .......... 260/112.5 R
4,086,196 4/1978 Tregear ................. 260/112.5 R
4,369,138 1/1983 Lindall ................. 260/112.5 R

OTHER PUBLICATIONS

Chem. Abstr., vol. 97, (1982) 182837.
Chem. Abstr., vol. 91, (1979) 151634.
Derwent Abstr. J5-5113-753, 2/22/79.
Howard Rasmussen and Lyman C. Craig, "Parathyroid Hormone"; The Parathyroid Polypeptides; The Rockefeller Institute, New York, N.Y., *Recent Program Hormone Research*; 1962; pp. 269-295.
J. T. Potts, Jr., et al., "Synthesis of a Biologically Active N-Terminal Tetratriacontapeptide of Parathyroid Hormone": *Proceedings of the National Academy of Sciences*; vol. 8, No. 1, 1971, pp. 63-67.

*Primary Examiner*—Delbert R. Phillips
*Attorney, Agent, or Firm*—Young & Thompson

[57] ABSTRACT

A peptide of the formula

H—Ser—Val—Ser—Glu—Ile—Gln—Leu—Nle—His—Asn—

Leu—Gly—Lys—His—Leu—Asn—Ser—Nle—Glu—Arg—Val—

Glu—Trp—Leu—Arg—Lys—Lys—Leu—Gln—Asp—Val—His—

Asn—A—NH₂ wherein A is Tyr or Phe, or a pharmaceutically acceptable salt thereof, is useful for the diagnosis of parathyroid gland function. When A is Tyr, the peptide can be labelled with iodine-125 without losing its PTH activity and without undergoing oxidation upon storage.

2 Claims, No Drawings

[NLE⁸, NLE¹⁸, TYR³⁴ OR PHE³⁴]-H-PTH PEPTIDE DERIVATIVES

This invention relates to novel human parathyroid hormone (h-PTH) peptide derivatives. More particularly, the present invention pertains to [Nle⁸, Nle¹⁸, Tyr³⁴]-h-PTH(1-34)NH₂ and [Nle⁸, Nle¹⁸, Phe³⁴]-h-PTH(1-34)NH₂, which are useful drugs for the treatment of hypoparathyroidism or PTH-related diseases. These compounds are represented by the formula

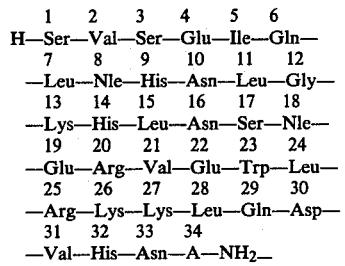

wherein A is Tyr or Phe, or a pharmaceutically acceptable salt thereof.

The present invention also comprises an iodine-125 labelled radioactive compound of peptide [I] wherein A is Tyr, because of its usefulness for the diagnosis of parathyroid gland function. Human parathyroid hormone is a peptide hormone consisting of 84 amino acids, and its biological activity is revealed by the 34-amino acid residue of its N-terminal residue, namely h-PTH(1-34) [Proc. Nat. Acad. Sci., U.S.A., 68, 63-67 (1971)]. However h-PTH is unstable due to existing L-methionine (Met), and loses its hormonal activity when labelled with iodine-125. [Recent Prog. Hormone Res., 18, 269-295 (1962)].

In order to overcome this disadvantage, h-PTH peptide derivatives have been proposed, having PTH activity, such as [Nle⁸, Nle¹⁸]-h-PTH [Jap. Pat. Unexam. Publ. No. 55-113753] and h-PTH(1-34)NH₂ [Jap. Pat. Unexam. Publ., No. 58-96052], in which L-methionine at position-8 and -18 is replaced by L-norleucine. However, even these have the disadvantages that the PTH activity of [Nle⁸, Nle¹⁸]-h-PTH(1-34) is approximately equal to but no more than that of natural h-PTH; and h-PTH(1-34) is also susceptible to oxidation due to having methionine in its molecule.

We have investigated h-PTH peptide derivatives with greater activity and stability. We have found that the above peptide [I], namely [Nle⁸, Nle¹⁸, Tyr³⁴]-h-PTH(1-34)NH₂ or [Nle⁸, Nle¹⁸, Phe³⁴]-h-PTH(1-34)NH₂, not only has a stronger affinity for PTH receptors as compared with known h-PTH(1-34) and [Nle⁸, Nle¹⁸]-h-PTH(1-34) and approximately 1.5-2 times stronger h-PTH activity, but also has immune activity and stability. The compound [I] of the present invention is a useful drug for the treatment of hypoparathyroidism or PTH-related bone diseases.

Furthermore, according to the prior assay method for h-PTH, in order to assay the peptide fragment having h-PTH activity, a specific antibody against antigen of h-PTH(1-34) has been prepared. However, as explained hereinabove, there are the disadvantages that h-PTH(1-34) is unstable due to having L-methionine and hence when labelled with iodine-125, methionine at position-8 and -18 is oxidized and the compound loses hormonal activity. Then an h-PTH derivative having PTH activity, invariant activity after treatment with anti-PTH antigen, stable hormonal activity when labelled with iodine-125 and stable radioactivity, [Nle⁸, Nle¹⁸, Tyr³⁴]-h-PTH(1-34) wherein methionine at position-8 and -18 is replaced by L-norleucine and L-phenylalanine at position-34 is replaced by L-tyrosine, was found. [Jap. Pat. Unexam. Publ. No. 55-113753]. The said peptide retains its activity upon labelling with iodine-125 because no methionine is in its molecule; however, its hormonal activity is only approximately equal to that of natural h-PTH(1-34).

We have found that the peptide [I] of the present invention [Nle⁸, Nle¹⁸, Tyr³⁴]-h-PTH(1-34)NH₂, in which A is the peptide [I] hereinabove is Tyr, retains its PTH activity after labelling, has two times higher radioactivity as compared with that of [Nle⁸, Nle¹⁸, Tyr³⁴]-h-PTH(1-34) and retains its biological activity in long term storage, and hence is a useful, easily labelled peptide for the diagnosis of parathyroid gland function.

The peptide [I] of the present invention can be synthesized as follows:

A carboxyl group of C-terminal tyrosyl or phenylalanyl is converted to amide, and a protected amino acid and/or lower peptide is reacted by liquid phase condensation in the order of the amino acid sequence of formula [I], and the protective group for the N-terminal amino group and side chain reactive group is released at the final stage of the reaction by acid decomposition.

The condensation reaction can be carried out by conventional peptide synthesis, i.e., repeating the attaching and removal of the protective groups and condensation. The protective groups for the synthesis of the starting materials or intermediates are conventional protective groups for peptide synthesis and are easily removable by hydrolysis, acid decomposition, reduction, aminolysis or hydrazinolysis.

For example, the amino group may be protected conventionally by an acyl group such as formyl, trifluoroacetyl, phthaloyl, p-toluenesulfonyl or o-nitrophenylsulfonyl group; a benzyloxycarbonyl group such as benzyloxycarbonyl, o-bromobenzyloxycarbonyl, p-bromobenzyloxycarbonyl, o- (or p-) chlorobenzyloxycarbonyl, p-nitrobenzyloxycarbonyl or p-methoxybenzyloxycarbonyl, an aliphatic oxycarbonyl group such as trichloroethyloxycarbonyl, t-amyloxycarbonyl, t-butoxycarbonyl or diisopropylmethoxycarbonyl, or an aralkyloxycarbonyl group such as 2-phenyl-isopropoxycarbonyl, 2-tolylisopropoxycarbonyl or 2-p-diphenylisopropoxycarbonyl. These amino groups can be protected by forming enamin reacted with 1,3-diketone such as benzoylacetone or acetylacetone.

The carboxyl group can be protected by amide formation, hydrazide formation or esterification. The amide group is substituted with a 3,4-dimethoxybenzyl or bis-(p-methoxyphenyl)methyl group. The hydrazide group is substituted with a benzyloxycarbonyl, trichloroethyloxycarbonyl, trifluoroacetyl, t-butoxycarbonyl, trityl or 2-p-diphenylisopropoxycarbonyl group. The ester group is substituted with an alkanol such as methanol, ethanol, t-butanol or cyanomethylalcohol; an aralkanol such as benzylalcohol, p-bromobenzylalcohol, p-chlorobenzylalcohol, p-methoxybenzylalcohol, p-nitrobenzylalcohol, 2,6-dichlorobenzylalcohol, benzhydrylalcohol, benzoylmethylalcohol, p-bromobenzoylmethylalcohol or p-chlorobenzoylmethylalcohol; a phenol such as 2,4,6-trichlorophenol, 2,4,5-trichlorophenol, pentachlorophenol, p-nitrophenol or 2,4-dinitrophenol; or a thiophenol such as thiophenol or p-nitrothiophenol. The hydroxy group is serine, or tyrosine may optionally be protected by esterification or etherification. A group protected by esterification is, for example, an acetyl group, a benzoyl group, benzoyloxycarbonyl or ethyloxycarbonyl. A group protected by etherification is, for example, a benzyl, 2,6-dichlorobenzyl, tetrahydropyranyl or t-butyl group. Protection of the hydroxy group can be effected by a 2,2,2-trifluoro-1-t-butyloxycarbonylaminoethyl or 2,2,2-trifluoro-1-benzyloxycarbonylaminoethyl group. However it is not always necessary to protect these hydroxy groups.

The amino group in the guanidino group in arginine can be protected by a nitro, tosyl, benzyloxycarbonyl or methylene-2-sulfonyl group. However it is not always necessary to protect the guanidino group.

The imino group in histidine can be protected by a benzyl, trityl, benzyloxycarbonyl, tosyl, 2,2,2-trifluoro-1-benzyloxycarbonylaminoethyl group, although the imino group does not always require protection.

In the present invention, preferable protective groups are t-butyloxycarbonyl and t-amyloxycarbonyl for $\alpha$-amino groups, o-chlorobenzyloxycarbonyl for side chain amino groups, i.e. $\epsilon$-amino in lysine, benzyl ester, ethyl ester and phenacyl ester for $\alpha$-carboxyl groups, benzyl ester for side-chain carboxyl groups, i.e. glutamate and aspartate, benzyl group for the hydroxyl group in serine, 2,6-dichlorobenzyl for the hydroxyl group in tyrosine and tosyl or methylene-2-sulfonyl for the amino group in guanidino of arginine.

The peptide [I] is synthesized by the condensation of amino acids or lower peptides. For example, an amino acid or peptide having a protected $\alpha$-amino group and an activated terminal carboxyl group is reacted with an amino acid or peptide having a free $\alpha$-amino group and a protected terminal carboxyl group. On the other hand, an amino acid or peptide having an activated $\alpha$-amino group and protected terminal carboxyl group is reacted with amino acid or peptide having a free terminal carboxyl group and a protected $\alpha$-amino group.

The carboxyl group can be activated by, for example, an acid azide, acid anhydride, acid imidazolide or active ester, such as by convertion to cyanomethyl ester, thiophenylester, p-nitrophenylester, p-nitrothiophenylester, 2,4-dinitrophenylester, 2,4,5-trichlorophenylester, 2,4,6-trichlorophenylester, pentachlorophenylester, N-hydroxysuccinimide ester, N-hydroxyphthalimido ester, carbodiimide such as N,N'-dicyclohexylcarbodiimide, N-ethyl-N'-3-dimethylaminopropylcarbodiimide, N,N'-carboxyldiimidazol or an isoxazolium salt such as Woodward reagent.

The preferred condensation reactions are the azide, active ester and carbodiimide methods. In the condensation reaction, racemization should carefully be avoided, and the preferred methods are the azide, the active ester method, or the Wünsch method [Z. Naturforsch., 216, 426 (1966)] or the Geiger method [Chem. Ber., 103, 788 (1970)], especially using N-ethyl-N'-3-dimethylaminopropyl-carbodiimide (WSCI) as a condensation agent.

The process of the present invention is preceded by a condensation reaction in the amino acid sequence of the formula [I]. It is preferable to synthesize from the C-terminal end of the molecule.

For example, it is preferable to synthesize the C-terminal fragment having amino acid sequence 29–34 with peptide fragment sequence 23–28. Preferable condensation of the C-terminal fragment with hexapeptide 23–28 is carried out by a modified Geiger method using WSC. Condensation of the obtained C-terminal fragment 23–24 with the peptide fragment having amino acid sequence 18–22 is preferably proceeded by a modified Geiger method using WSC. The resulting C-terminal fragment 18–34 is connected one by one with a peptide fragment of sequence 13–17, a peptide fragment 8–12 and a peptide fragment 1–7.

In the above condensation reaction, protective groups for the $\alpha$-amino groups, for example t-butyloxycarbonyl and t-amyloxycarbonyl, are removed by trifluoroacetice acid. A protective group for $\alpha$-carboxyl, for example ethyl ester, is hydrolyzed by diluted sodium hydroxide solution or is converted to protected hydrazide such as hydrazide or trichloroethoxycarbonyl hydrazide. Phenacyl ester is decomposed by Zn powder in acetic acid, and benzyl ester is removed by anhydrous hydrogen fluoride or hydrogenation, or is converted to hydrazide.

Thus the tetratriacontapeptide having protected N-terminal $\alpha$-amino group, $\epsilon$-amino group, side chain carboxyl, guanidino and/or hydroxyl can be obtained. The protective groups are preferably split by acid decomposition such as one-step removal with anhydrous hydrogen fluoride or trifluoromethane sulfonate to obtain the corresponding compound of formula [I].

The resulting peptide [I] can be purified by known purification methods for peptide or protein. For example, it can be purified by gel filtration using Sephadex G-25, Sephadex G-50 or Sephadex LH-20 (all trade names), column chromatography using carboxy methyl cellulose or ion-exchange resin, or high performance liquid chromatography.

The peptide [I] of the present invention can be obtained in the form of free base or its pharmaceutically acceptable salt, e.g. its salt with an inorganic or organic base such as formate, acetate, propionate, glycolate, succinate, malate, tartrate or citrate.

The peptide [I] can form a complex on addition of an inorganic or organic substance. The said complex is an unknown complex which can retard the activity of the peptide. For example, an inorganic compound derived from calcium, magnesium, aluminum, cobalt or zinc, and especially the slightly soluble salts thereof such as phosphate, pyrophosphate or polyphosphate, and hydroxide, or polyphosphates of alkaline metals combine with the peptide [I] to form such a complex.

The peptide [I], i.e. [$Nle^8$, $Nle^{18}$, $Tyr^{34}$]-h-PTH(1–34)$NH_2$ is useful as a labelled compound for radio immunoassay. For example, the above peptide [I] and chloramine T were added by aliquot to radioactive iodine-125 in a phosphate buffer (pH 7.1), the mixture was stirred, sodium bisulfide was added, and a small amount of potassium iodide and serum albumin were also added. Iodine-125 labelled fractions were collected by chromatography to obtain an iodine-125 conjugated compound.

The PTH activity of the peptide [I] and iodine-125 labelled radioactive compound is shown below.

(1) Labelling with iodine-125:

A solution (10 $\mu$l) of h-PTH(1–34) (2 $\mu$g), h-PTH(1–34)$NH_2$ 2 $\mu$g), [$Nle^8$, $Nle^{18}$, $Tyr^{34}$]-h-PTH(1–34) (2 $\mu$g) or [$Nle^8$, $Nle^{18}$, $Tyr^{34}$]-h-PTH(1–34)$NH_2$ (2 $\mu$g) and a solution (20 $\mu$l) of chloramine T (3.5 mg/ml) were added to 0.5 M phosphate buffer (pH 7.1, 50 $\mu$l) containing iodine-125-NaI (radioactivity; 2 mCi), the mixture was stirred for 30 seconds and sodium bisulfide (4.5 mg/ml) solution (50 μl) was added to stop the reaction. A 0.1 N acetic acid solution (0.5 ml) containing 5% human serum albumin was added thereto and the mixture was charged on a column (1×50 cm) of Sephadex G-10, then eluted with the 0.1 N acetic acid solution to obtain labelled compounds.

[Assay of PTH activity]

(1) Preparation of PTH receptor:

Rats, strain SD, male, weight 200-250 g, were decollated to bleed, laparotomized and excised of kidneys. A surface membrane was removed, and the renal cortex carved out and ice-cooled. The following operations should be carried out at a temperature as low as possible (0°-4° C.).

The renal cortex was immersed in a solution (hereinafter designated as solution A) of 10 mM Tris-HCl buffer (pH 7.5) containing 0.25 M sucrose and 1mM EDTA. Three times the volume of solution A (ml) suspending the renal cortex (wet weight) was added to a renal cortex in a glass tube with Tefron (trade name) pestle and homogenized.

A homogenate was centrifuged for 10 minutes at 150×g, and the supernatant solution was further centrifuged for 15 mins. at 2200×g. The supernatant solution was discarded and the upper emulsion part of precipitate was suspended in a solution A. The said emulsion was centrifuged for 15 mins. at 2200×g. The precipitate was again suspended and frozen at −70° C. in a bottle stored at −20° C.

(2) Reaction with PTH and PTH-receptor:

Specimen was dissolved in 100 mM Tris-HCl buffer (ph 7.5) containing ATP-Mg 2 mM, $MgCl_2$ 10 mM, KCl 60 mM, GTP 20 μM, isobutyl methyl xanthine 1 mM, creatine phosphate 8 mM and bovine serum albumin (BSA) 0.2% to prepare 2 μg/ml and 10 μg/ml solutions. Standard bovine PTH(1-34) solution was also prepared in the same manner.

The above solutions [2 μg/ml and 10 μg/ml specimen] and bovine PTH(1-34) (50 μl) were each divided among eight glass test tubes, and kept in ice water in order to prevent ATP formation and to prepare test solutions. A stock solution of PTH receptor stored at −20° C. was thawed to room temperature. Creatine kinase, previously dissolved in solution A, was added thereto to prepare creatine kinase at 0.1 mg/ml and PTH receptor at 1.4 mg/ml as protein by adding solution A while keeping the solution in ice cooling. After the above test solutions were preincubated at 37° C. for several minutes, the PTH receptor-creatine kinase solution (each 50 μl) was added therein and incubated at 37° C. for 10 mins. 0.1 M acetate buffer (pH 4.0, 100 μl) was added, the mixture immediately placed in ice-water, and the tube heated in boiling water for one minute to stop the reaction.

(3) Assay of generated c-AMP:

Distilled water was added to the above reaction-stopped solution to 10-30 times dilution, and deproteinized by centrifugation for 15 mins. at 2000×g. An amount of c-AMP in a supernatant solution was assayed by RIA-kit (YASAMA SHOYU CO.)

(4) Determination of PTH activity:

The measured values of c-AMP hereinabove were converted to a unit of pM (pico mole)/mg PTH receptor-protein/minute as a designation of measured value. The measured value of the specimen was compared to the standard substance according to a parallel assay line two by two.

(5) PTH activity (U/mg):

| Sample | PTH Activity | PTH Activity After Labelling with $^{125}I$ |
|---|---|---|
| h-PTH | 3000 | >100 |
| h-PTH(1-34)$NH_2$ | 5100 | >150 |
| [$Nle^8$, $Nle^{18}$, $Tyr^{34}$]-h-PTH(1-34) | 2930 | 2480 |
| [$Nle^8$, $Nle^{18}$, $Tyr^{34}$]-h-PTH(1-34)$NH_2$ | 5030 | 5000 |
| [$Nle^8$, $Nle^{18}$, $Phe^{34}$]-h-PTH(1-34)$NH_2$ | 5000 | — |

The abbreviations used herein have the following meanings:

| | | | |
|---|---|---|---|
| Boc: | t-butyloxycarbonyl | Aoc: | t-amyloxycarbonyl |
| OPAC: | phenacyl ester | Z-Cl: | o-chlorobenzyloxycarbonyl |
| Bzl: | benzyl | | |
| Val: | L-valine | Tos: | tosyl |
| OEt: | ethyl ester | Ile: | L-isoleucine |
| OBzl: | benzyl ester | ONP: | p-nitrophenyl ester |
| Trp: | L-tryptophan | Nle: | L-norleucine |
| Ser: | L-serine | Phe: | L-phenylalanine |
| Asn: | L-aspartic acid | Glu: | L-glutamic acid |
| Leu: | L-leucine | Z(OMe): | p-methoxybenzyloxycarbonyl |
| $Bzl-Cl_2$: | 2,6-dichlorobenzyl | | |
| Arg: | L-arginine | Asp: | L-aspartic acid |
| DCHA: | dicyclohexylamine | Gly: | glycine |
| Lys: | L-lysine | Gln: | L-glutamine |
| NaOH: | sodium hydroxide | His: | L-histidine |
| Tyr: | L-tyrosine | DMSO: | dicyclohexylamine |
| TosOH: | p-toluenesulfonic acid | DCC: | N,N'—dicylohexyl-carbodiimide |
| TFA: | trifluoroacetic acid | $Et_3N$: | triethylamine |
| THF: | tetrahydrofuran | ether: | diethyl ether |
| NMM: | N'—methylmorpholine | DMF: | dimethylformamide |
| WSC: | N—ethyl-N'—di-methylaminopropyl-carbodiimide | TBA: | t-butylamine |
| | | HOBt: | 1-hydroxybenzotriazole |

PF( ): PF means protected amino acid or peptide fragment.
Numbers in ( ) mean series of amino acid sequence in the formula [I].

The following examples illustrate the present invention. In the examples, the following carriers and developing solvents for thin layer chromatography (TLC) are used:
Carrier: Silica gel G.
Developer:
 1. Chloroform-methanol-acetic acid (95:5:3)
 2. Chloroform-methanol-acetic acid (85:15:5)
 3. Chloroform-methanol-acetic acid (80:25:2)
 4. Chloroform-ethanol-ethyl acetate (5:2:5)
 5. Hexane-ethyl acetate (1:1)
Carrier: Merck cellulose. (DC-Alufolien)
Developer: 6. Butanol-pyridine-acetic acid-water (2:2:2:3) (upper layer)

[Amino acid analysis]

Unless specified, the sample is hydrolyzed in 6 N HCl at 110° C. for 24-48 hours in a sealed tube.

EXAMPLE 1

Preparation of [$Nle^8$, $Nle^{18}$, $Tyr^{34}$]-h-PTH(1-34)$NH_2$ (1) PF(34): Boc-Tyr(Bzl-$Cl_2$)-$NH_2$ [1]

DCC (24.76 g, 0.12 M) in dry THF was added dropwise at −5° C. to Boc-Tyr(Bzl-$Cl_2$)-OH (52.84 g, 0.12 M) and p-nitrophenol (16.6 g, 0.12 M) dissolved in dry THF, then the mixture was stirred overnight. The precipitates were removed, and the filtrate solution was saturated with $NH_3$ gas and stirred for 5 hours. Further precipitates were dissolved by adding DMF and the material was concentrated in vacuo. The residue was crystallized from ether, filtered and dried to obtain the product [1].

Yield: 44.77 g (yield: 84.9%).
m.p.: 214–216° C.
TLC: $Rf_1 = 0.62$.
Elementary analysis $[C_{21}H_{24}O_4N_2Cl_2]$:

|  | C % | H % | N % |
|---|---|---|---|
| Calculated: | 57.41 | 5.51 | 6.38 |
| Found: | 57.42 | 5.59 | 6.51 |

$[\alpha]_D^{25}$: −5.54° (c=1, DMF).

(2) PF(33–34): Boc-Asn-Tyr(Bzl-Cl$_2$)-NH$_2$ [2]

TFA (100 ml) was added with ice cooling to the compound [1] (26.36 g, 60 mM) dissolved in methylene chloride, and the mixture was stirred at room temperature for 30 mins. Methylene chloride and TFA were removed in vacuo. The residue was crystallized from ether, filtered and dried. WSC (10.98 ml, 60 mM) was added at −15° C. to the obtained crystals, as were also Boc-Asn-OH (13.93 g, 60 mM) and HOBt (8.1 g, 60 mM) dissolved in DMF, and the mixture was stirred overnight. The precipitates were collected by filtration, washed with 5% aq. sodium bicarbonate, water (twice) and methanol, in this order, and dried to obtain the product [2]. The mother liquor thereof was distilled in vacuo to remove DMF and the resulting crystals were washed with water and methanol, then dried to obtain the product [2] which was combined with the above product.

Yield: 28.64 g (yield: 86.25%).
m.p.: 240–242° C.
$[\alpha]_D^{25}$: −24.06° (c=1, DMF).
Elementary analysis $[C_{25}H_{30}O_6Cl_2]$:

|  | C % | H % | N % |
|---|---|---|---|
| Calculated: | 54.25 | 5.46 | 10.13 |
| Found: | 54.46 | 5.38 | 10.31 |

(3) PF(32–34): Boc-His(Tos)-Asn-Tyr(Bzl-Cl$_2$)—NH$_2$ [3]

TFA (100 ml) was added with ice cooling to the compound [2] (22.14 g, 40 mM) dissolved in a small amount of methylene chloride. The mixture was stirred at room temperature for 30 mins. and the TFA was removed in vacuo to obtain the de-Boc compound.

BocHis(Tos)-OH.DCHA (28.36 g, 48 mM) suspended in ethyl acetate (500 ml) was washed with 1 N H$_2$SO$_4$ (twice) and water (twice), dried with anhydrous sodium sulfate and the ethyl acetate was removed in vacuo. The de-Boc compound hereinabove dissolved in dry DMF and HOBt (6.48 g, 48 mM) was added to the residue dissolved in DMF, then WSC (8.78 ml, 48 mM) was added thereto at −15° C. and the mixture was stirred at room temperature overnight. After the reaction was complete, the DMF was removed in vacuo and the residue was washed with 5% aq. sodium bicarbonate and twice with water, then dried to obtain the crude product, which was recrystallized from methanol-ether to obtain the product [3]. The mother liquor was concentrated in vacuo, and the residue was crystallized from methanol-hexane to obtain the compound [3]. which was combined with the product [3] hereinabove.

Yield: 28.81 g (yield: 85.1%).
m.p.: 170–175° C.
TLC: $Rf_3 = 0.68$, 0.42 (the Tos was partially removed).
Elementary analysis $[C_{38}H_{44}O_9N_7Cl_2S]$:

|  | C % | H % | N % |
|---|---|---|---|
| Calculated: | 53.96 | 5.24 | 11.59 |
| Found: | 53.03 | 5.65 | 12.04 |

(4) PF(31–34): Boc-Val-His-Asn-Tyr(Bzl-Cl$_2$)-NH$_2$ [4]

TFA (120 ml) was added with ice cooling to the compound [3] (28.81 g, 34.06 mM) dissolved in a small amount of methylene chloride. The mixture was stirred at room temperature for 30 mins. and TFA was removed in vacuo. Ether was added to the residue and the precipitated crystals were collected by filtration, dried, then dissolved in DMF (140 ml). The solution was neutralized with NMM. A solution of Boc-Val-OH (8.14 g, 37.47 mM) and HOBt (5.06 g, 37.47 mM) dissolved in DMF (60 ml) was added thereto, thereafter WSC (6.86 ml, 37.47 mM) was added at −15° C. and the mixture was stirred at room temperature overnight. DMF was removed in vacuo and the residue was washed with 5% aqueous sodium bicarbonate, and three times with water, to obtain the product [4].

Yield: 27.76 g (yield: 103.2%).
m.p.: 164°–166° C.
TLC: $Rf_3 = 0.65$.
$[\alpha]_D^{25}$: −29.38° (c=1, DMF).
Elementary analysis $[C_{36}H_{46}O_8Cl_2]$:

|  | C % | H % | N % |
|---|---|---|---|
| Calculated: | 54.75 | 5.87 | 14.19 |
| Found: | 53.37 | 5.78 | 13.43 |

(5) PF(30–34): Boc-Asp(OBzl)-Val-His-Asn-Tyr(Bzl-Cl$_2$)-NH$_2$[5]

TFA (110 ml) was added with ice cooling to the compound [4] (27.76 g, 35.15 mM) suspended in a small amount of methylene chloride. The mixture was stirred at room temperature for 30 mins. and TFA was removed in vacuo. Ether was added to the residue and the precipitated crystals were collected by filtration, dried, then dissolved in DMF (120 ml). The solution was neutralized by adding NMM (10 ml). Boc-Asp(OBzl)-OH (12.5 g, 38.67 mM) and HOBt (5.22 g, 38.67 mM) dissolved in dry DMF (80 ml) were added thereto, and the mixture was stirred at room temperature overnight. DMF was removed in vacuo, and the residue was washed with 5% aqueous sodium bicarbonate, and twice with water, and was thereafter suspended in methanol. Methanol was added to recrystallize the product [5].

Yield: 31.42 g (yield: 89.8%).
m.p.: 214°–215° C.
TLC: $Rf_3 = 0.6$.
$[\alpha]_D^{25}$: −23.28° (c=1, DMF).
Elementary analysis $[C_{47}H_{57}O_{11}N_9Cl_2]$:

|             | C %   | H %  | N %   |
| ----------- | ----- | ---- | ----- |
| Calculated: | 56.74 | 5.78 | 12.67 |
| Found:      | 56.19 | 5.79 | 12.07 |

(6) PF(29–34): Boc-Gln-Asp(OBzl)-Val-His-Asn-Tyr(Bzl-Cl$_2$)-NH$_2$ [6]

TFA (120 ml) was added to the compound [5] (31.11 gm, 31.27 mM) suspended in methylene chloride. The mixture was stirred at room temperature for 30 mins. and TFA and methylene chloride were removed in vacuo. Ether was added to the residue. The precipitated crystals were collected by filtration, dried and dissolved in dry DMF (100 ml). The solution was neutralized by NMM (8 ml). A solution of Boc-Gln-ONP (12.64 g, 34.4 mM) and HOBt (0.42 g, 3.13 mM) dissolved in dry DMF was added thereto, followed by the addition of NMM (3.78 ml) with ice cooling. The resulting mixture was stirred overnight. After the reaction was complete, DMF was removed in vacuo, the residue was washed with 5% aqueous sodium bicarbonate and twice with water, suspended in methanol and recrystallized from methanol to obtain the product [6].

Yield: 33.19 g (yield: 94.5%).
m.p.: 81°–83° C.
TLC: Rf$_3$=0.47.
[α]$_D^{24}$: −23.98° (C=1, DMF).
Elementary analysis [C$_{52}$H$_{65}$O$_{13}$N$_{11}$Cl$_2$]:

|             | C %   | H %  | N %   |
| ----------- | ----- | ---- | ----- |
| Calculated: | 55.61 | 5.83 | 13.72 |
| Found:      | 54.81 | 5.96 | 13.07 |

Amino acids analysis: Asp 2.19 (2), Glu 1.05 (1), Val 1 (1), Tyr 0.73 (1), His 0.85 (1).

(7) PF(27–28): Boc-Lys(Z-Cl)-Leu-Oet [7]

Boc-Lys(Z-Cl)-OH.TBA (97.6 g, 0.2 M) suspended in ethyl acetate (500 ml) was washed with 1N-HCl and water, dried with anhydrous sodium sulfate and concentrated in vacuo to an oily material. The oily material was dissolved in dry THF (500 ml), and H-Leu-OEt.HCl (39.14 g, 0.2 M) and HOBt (27.0 g, 0.2 M) were added thereto. WSC (36.6 ml, 0.2 M) was also added at −15° C. and the mixture was stirred at room temperature overnight. THF was removed in vacuo. The resulting residue dissolved in ethyl acetate (600 ml) was washed with 5% aqueous sodium bicarbonate, water, 1N HCl and water, in this order, dried with anhydrous sodium sulfate and concentrated in vacuo. The residue was cooled to crystallize the substance, then hexane was added thereto, and the substance filtered to obtain the product [7].

Yield: 110.62 g (yield: 99.5%).
m.p.: 77°–80° C.
TLC: Rf$_5$=0.48.
[α]$_D^{29}$ −9.08° (c=1, DMF).

(8) PF(26–28): Boc-Lys(Z-Cl)-Lyz(Z-Cl)-Leu-OEt [8]

The compound [7] (110.62 g, 0.199 M) was added to methylene chloride (50 ml). TFA (250 ml) was added thereto with ice cooling. The mixture was stirred at room temperature for 1 hour. TFA and methylene chloride were removed in vacuo to obtain an oily de-Boc compound.

Boc-Lys(Z-CL)-OH.TBA (97.1 g, 0.199 M) suspended in ethyl acetate (500 ml) was washed with 1N HCl (300 ml) and water, dried with anhydrous sodium sulfate and concentrated in vacuo to obtain an oily substance. The above de-Boc compound and HOBt (26.9 g, 0.199 M) dissolved in dry THF (250 ml) were added to the above oily substance dissolved in dry THF (150 ml). WSC (36.4 ml, 0.199 M) was added dropwise at −15° C. thereto and the resulting mixture was stirred at room temperature overnight. THF was removed in vacuo to precipitate agar-like crystals, which were dissolved in ethyl acetate, washed with 5% aqueous sodium bicarbonate, water, 1N HCl and water, in this order, dried with anhydrous sodium sulfate, and concentrated in vacuo. The precipitate was treated with hexane and filtered, then recrystallized from ethyl acetate-ether-hexane to obtain the product [8].

Yield: 156.52 g (yield: 92.2%).
m.p.: 114°–116° C.
TLC: Rf$_2$=0.78.
[α]$_D^{29}$: −20.72° (c=1, DMF).

(9) PF(25–28): Aoc-Arg(Tos)-Lys(Z-Cl)-Lys(Z-Cl)-Leu-OEt [9]

TFA (2500 ml) was added with ice cooling to the compound [8] (156.5 g, 184 mM) dissolved in methylene chloride (50 ml). The mixture was stirred at room temperature for 1 hour. The reaction mixture was concentrated in vacuo, and the residue dissolved in dry DMF (300 ml) was neutralized with NMM. Aoc-Arg(Tos)-OH (86.0 g, 202 mM) dissolved in dry DMF (100 ml) and HOBt (27.3 g, 202 mM) were added thereto, and WSC (37.0 ml, 202 mM) was added dropwise at −15° C. thereto, then the mixture was stirred at room temperature overnight. DMF was removed in vacuo and the residue was dissolved in ethyl acetate (1 lit.) The solution was washed with 5% aqueous sodium bicarbonate, saturated NaCl solution, twice with 1N HCl and saturated sodium chloride solution, dried with anhydrous sodium sulfate and concentrated in vacuo. Ether was added to the residue and the residue was filtered to obtain the product [9].

Yield: 217.91 g (yield: 100.6%).
TLC: Rf$_1$=0.09, Rf$_2$=0.67.
m.p.: 75°–78° C.
[α]$_D^{28}$: −14.02° (c=1, DMF).

(10) PF(24–28): Boc-Leu-Arg(Tos)-Lys(Z-Cl)-Lys(Z-Cl)-Leu-OEt [10]

Methylene chloride (100 ml) and TFA (250 ml) were added to the compound [9] (217.9 g, 0.185 M). The mixture was stirred at room temperature for 80 mins. and methylene chloride and TFA were removed in vacuo. The obtained oily material was dissolved in dry DMF (300 ml) and neutralized by adding NMM. Boc-Leu-OH. H$_2$O) (50.9 g, 0.204 M) and HOBt (27.6 g, 0.204 M) dissolved in dry DMF (100 ml) were added thereto, and WSC (37.3 ml, 0.204 M) was added dropwise at −15° C., then the resulting mixture was stirred at room temperature overnight. DMF was removed in vacuo and the residue was added to water. The precipitated product was filtered, and recrystallized twice from methanol-ether-hexane to obtain the product [10].

Yield: 213.63 g (yield: 90.5%).
m.p.: 157°–160° C.
TLC: Rf$_1$=0.28, Rf$_2$=0.77.
[α]$_D^{27}$: −18.68° (c=1, DMF).

(11) PF(23–28):
Boc-Trp-Leu-Arg(Tos)-Lys(Z-Cl)-Lys(Z-Cl)-Leu-OEt [11]

Methylene chloride (100 ml) and TFA (250 ml) were added to the compound [10] (153.17 g, 0.12 M). The mixture was stirred at room temperature for 80 mins. and methylene chloride and TFA were removed in vacuo. The residue was dissolved in dry DMF (250 ml) and neutralized by adding NMM. HOBt (17.84 g, 0.132 M) and Boc-Trp-OH (40.17 g, 0.132 M) were added thereto, and WSC (24.2 ml, 0.132 M) was added dropwise at $-15°$ C., then the mixture was stirred at room temperature overnight. DMF was removed in vacuo and the residue was poured into 5% aqueous sodium bicarbonate (5 lit.) The precipitated substance was filtered and suspended in water to filter again, then recrystallized twice from methanolether to obtain the product [11].

Yield: 142.57 g (yield: 81.2%).
m.p.: 168°–170° C.
TLC: $Rf_1 = 0.31$, $Rf_2 = 0.82$.
$[\alpha]_D^{28}$: $-18.64°$ (c=1, DMF).

(12) PF(23–28):
Boc-Trp-Leu-Arg(Tos)-Lys(Z-Cl)-Lys(Z-Cl)-Leu-OH [12]

The compound [11] (140.64 g, 96.16 mM) was dissolved in hot ethanol (1200 ml). After cooling, a small amount of precipitate was filtered off, aqueous 1N-NaOH (288 ml, 3 molar equivalents was added and the resulting mixture was stirred at room temperature for 1 hour. 1N Tos.OH solution (192 ml, 2 molar equivalents) was added to the reaction mixture, filtered and ethanol was removed in vacuo. 1N Tos.OH (96 ml, 1 molar equivalent) was added thereto, water (2 lit.) was added and the precipitate was filtered and dried to obtain the product [12].

Yield: 142.98 g (yield: 101.1%).
TLC: $Rf_2 = 0.71$.
m.p. 125°–130° C.
$[\alpha]_D^{27}$: $-37.24°$ (c=1, DMF).
Elementary analysis $[C_{69}H_{94}O_{15}N_{12}SCl_2 \cdot 2H_2O]$:

|  | C % | H % | N % |
|---|---|---|---|
| Calculated: | 56.35 | 6.72 | 11.43 |
| Found: | 56.03 | 6.62 | 11.85 |

Amino acid analysis: Leu 2 (2), Lys 2.08 (2), Arg 1.10 (1), Trp 0.83 (1).

(13) PF(23–34):
Boc-Trp-Leu-Arg(Tos)-Lys(Z-Cl)-Lys(Z-Cl)-Leu-Gln-Asp(OBzl)-Val-His-Asn-Tyr(Bzl-Cl$_2$)-NH$_2$ [13]

TFA (7 ml) was added with ice cooling to the compound (1.68 g, 1.5 mM) dissolved in small amount of methylene chloride. The mixture was stirred at room temperature for 30 mins. TFA was removed in vacuo, ether was added to the residue, and the precipitated crystals were filtered and dried. The crystals were dissolved in a small amount of dry DMF (30 ml) and neutralized with a small amount of NMM. The compound [12]0 (2.43 g, 1.65 mM), HOBt (0.22 g, 1.65 mM) and dry DMF (20 ml) were added thereto. WSC (0.3 ml, 1.1 molar equivalent) was added at $-15°$ C. and the mixture was stirred at room temperature overnight. DMF was removed in vacuo, and the residue was washed with 5% aqueous sodium bicarbonate and twice with water, suspended in methanol, ether added, and filtered and dried to obtain the prodcut [13].

Yield: 3.62 g (yield: 99.1%).
m.p.: 260°–270° C.
$[\alpha]_D^{25}$: $-46.6°$ (c=0.3, DMF).
Amino acid analysis: Asp 1.94 (2), Glu 0.96 (1), Val 0.71 (1), Leu 2.00 (2), Try 0.98 (1), Lys 2.09 (2), His 0.58 (1), Arg 0.91 (1), Trp 0.78 (1).

(14) PF(22): Boc-Glu(OBzl)-OPAC [14]

Phenacyl bromide (113.5 g, 0.57 M) was added with ice cooling to Boc-Glu(OBzl)-OH (128.2 g, 0.38 M) dissolved in DMF (600 ml). Et$_3$N (79.3 ml, 0.57 M) was added dropwise thereto, and the mixture was stirred at 30° C. for 4 hours. Potassium acetate (30 g) was added thereto, the mixture stirred for 45 mins. and DMF was removed in vacuo. Ethyl acetate (600 ml) was added to the residue, and the residue was then washed twice with 5% aqueous sodium bicarbonate and twice with water. The ethyl acetate layer was dried with anhydrous sodium sulfate and the solvent was removed in vacuo to precipitate the crystals. Hexane was added thereto and the crystals were filtered to obtain the product [14].

Yield: 156.19 g (yield: 90.2%).
TLC: $Rf_5 = 0.73$.

(15) PF(21–22): Boc-Val-Glu(OBzl)-OPAC [15]

Methylene chloride (50 ml) was added to the compound [14] (147.88 g, 0.325 M). TFA (300 ml) was added with cooling thereto, and the mixture was stirred at room temperature for 1 hour whereupon methylene chloride and TFA were removed in vacuo. Ether was added to the residue, and the precipitated crystals were filtered and dried. A solution of crystals dissolved in dry DMF (300 ml) was neutralized with NMM. HOBt (35.14 g, 0.26 M) and Boc-Val-OH (56.49 g, 0.26 M) were added to the solution, and WSC (47.6 ml, 0.26 M) was added at $-15°$ C. The mixture was stirred at room temperature for 2 days. DMF was removed in vacuo, and the residue dissolved in chloroform (500 ml) was washed with 5% aqueous sodium bicarbonate, water, 1N HCl and water. The chloroform layer was dehydrated by adding anhydrous sodium sulfate, the solvent was removed in vacuo, then the obtained crystals were filtered with addition of hexane and recrystallized from ethyl acetate-ether to obtain the product [15].

Yield: 106.97 g (yield: 74.2%).
TLC: $Rf_3 = 0.63$.
m.p.: 139°–141° C.
$[\alpha]_D^{29}$: $-18.92°$ (c=1, DMF).

(16) PF(20–22): Aoc-Arg(Tos)-Val-Glu(OBzl)-OPAC [16]

Methylene chloride (50 ml) was added to the product [15] (99.93 g, 0.18 M). TFA (200 ml) was added with ice cooling thereto. The mixture was stirred at room temperature for 1 hour and methylene chloride and TFA were removed in vacuo. Hexane was added to the residue, and the solvent was removed by decantation. Ether was added to the residue, then the ether was removed in vacuo. The obtained oily material dissolved in dry DMF (200 ml) was made neutral with NMM. HOBt (24.33 g, 0.18 M), Aoc-Arg(Tos)-OH (76.60 g 0.18 M) and dry DMF (200 ml) were added thereto, and WSC (32.94 ml, 0.18 M) was added at $-15°$ C., then the mixture was stirred at room temperature overnight. DMF was removed in vacuo and the residue was dissolved in ethyl acetate (1 lit.) The solution was washed with 5% aqueous sodium bicarbonate, water, 1N HCl and water, in this order, dried with anhydrous sodium sulfate, then ethyl acetate was removed in vacuo. The resulting oily substance was recrystallized from ethyl acetate-ether and the crystals were suspended. The same operation was repeated 3 times to obtain the product [16].

Yield: 149.75 g (yield: 94.6%).
TLC: $Rf_1=0.74$, $Rf_4=0.81$.
m.p.: 110°–114° C.
$[\alpha]_D^{29}$: −11.5° (c=1, DMF).

(17) PF(19–22):
Boc-Glu(OBzl)-Arg(Tos)-Val-Glu(OBzl)-OPAC [17]

Methylene chloride (50 ml) was added to the compound [16] (149.40 g, 0.170 M). TFA (300 ml) was added with ice cooling thereto. The mixture was stirred at room temperature for 1 hour, and methylene chloride and TFA were removed in vacuo. Ether was added to the residue, then the ether was removed in vacuo and the thus obtained oily material was dissolved in dry DMF (200 ml). HOBt (25.27 g, 0.187 M) and Boc-Glu(OBzl)-OH (63.09 g, 0.187 M) were added to the solution, followed by the addition of dry DMF (100 ml) and WSC (34.22 ml, 0.187 M) at −15° C. The mixture was stirred at room temperature overnight. Solvents were removed and the residue was poured into water (6 lit.), whereupon the precipitated crystals were collected by filtration. The crystals suspended in a methanol and ether mixture were filtered and dissolved in hot methanol. The precipitate was cooled and filtered and suspended again in methanol. The same procedure was repeated three times to obtain the compound [17]. Solvent was removed from the mother liquor and the solvated precipitate was recrystallized from methanol-ether to obtain the product (25.02 g).

Yield: 141.44 g (yield: 76.7%).
TLC: $Rf_1=0.56$, $Rf_4=0.82$.
m.p.: 119°–121° C.
$[\alpha]_D^{29}$: −12.9° (c=1, DMF).

(18) PF(18–22):
Boc-Nle-Glu(OBzl)-Arg(Tos)-Val-Glu(OBzl)-OPAC [18]

Methylene chloride and TFA (24 ml) were added to the compound [17] (6.51 g, 6 mM) with ice cooling. The mixture was stirred at room temperature for 40 mins., and methylene chloride and TFA were removed in vacuo. The residue was crystallized by the addition of ether and dried. The crystals were dissolved in dry DMF, and neutralized by adding NMM to pH 7 with ice cooling. Boc-Nle-OH (1.67 g, 7.2 mM) and HOBt (0.97 g, 7.2 mM) dissolved in dry DMF (40 ml) were added to the solution, and WSC (1.3 ml, 7.2 mM) was added at −15° C. thereto, then the mixture was stirred overnight. DMF was removed in vacuo, water added to the residue, and the precipitate was filtered and washed with 5% aqueous sodium bicarbonate, three times with water, three times with 1N HCl and methanol. The product [18] was recrystallized from methanol-ether.

Yield: 5.61 g (yield: 78%).
TLC: $Rf_1=0.56$.

(19) PF(18–22):
Boc-Nle-Glu(OBzl)-Arg(Tos)-Val-Glu(OBzl)-OH [19]

Zinc powder (8 g) was added to the compound [18] (5.03 g, 4.2 mM) dissolved in acetic acid (30 ml) and the mixture was stirred at room temperature for 5.5 hours. The zinc powder was filtered off and the acetic acid was removed in vacuo. The precipitated crystals were mixed with ether and filtered to obtain the product [19].

Yield: 4.42 g.
TLC: $Rf_1=0.18$, $Rf_2=0.67$.
m.p.: 210° C. (decomp.).
Amino acid analysis: Nle 1.01 (1), Glu 2.05 (2), Arg 0.98 (1), Val 1 (1).

(20) PF(18–34): Boc—Nle—Glu(OBzl)—Arg(Tos)—Val—

—Glu(OBzl)—Trp—Leu—Arg(Tos)—

—Lys(Z—Cl)—Lys(Z—Cl)—Leu—

—Gln—Asp(OBzl)—Val—His—Asn—

—Tyr(Bzl—Cl$_2$)—NH$_2$   [20]

Skatole (0.5 g, 3.5 mM), dimethylsulfide (25 ml), ethanedithiol (2.5 ml) and TFA (25 ml) were added to the compound [19] (8.9 g, 3.5 mM). The reaction mixture was stirred at 0° C. for 10 mins. and at room temperature for 45 mins., and then was concentrated in vacuo. Ether was added to the residue, and the precipitate was filtered, dried, dissolved in dry DMF (100 ml) and the resulting solution was neutralized with NMM to pH 7. HOBt (0.54 g, 4 mM) and the compound [19] (4.3 g, 4 mM) were added thereto. WSC (0.73 ml) was added at −15° C. to the mixture and stirred at room temperature for 2 days. DMF was distilled off in vacuo and 5% aqueous sodium bicaronate was added thereto. The precipitate was filtered and washed with water. The product was dissolved in ethanol and precipitated by adding water. The same operations were repeated two times to obtain the product [20].

Yield: 11.12 g (yield: 94%).
TLC: $Rf_3=0.72$.
m.p.: 250° C. (decomp.).
$[\alpha]_D^{28}$: −4.73° (c=0.53, DMF).
Amino acid analysis: Asp 1.98 (2), Glu 3.04 (3), Val 1.69 (2), Leu 2 (2), Tyr 1.07 (1), Lys 1.93 (2), His 0.59 (1), Arg 1.97 (2), Trp 0.35 (1), Nle 1.07 (1).

(21) PF(17): Boc-Ser(Bzl)-OPAC [21]

Phenacyl bromide (89.6 g, 0.45 M) was added to Boc-Ser(Bzyl)-OH (88.6 g, 0.3 M) dissolved in DMF (400 ml), and Et$_3$N (62.6 ml, 0.45 M) was added dropwise with ice cooling to the mixture. The new mixture was stirred at 30° C. for 3.5 hours. Potassium acetate (22.1 g, 0.225 M) was added to the reaction mixture and the mixture was stirred at room temperature for 1 hour. DMF was distilled off in vacuo and the residue was dissolved in ethyl acetate (500 ml), then the solution was washed with 5% aqueous sodium bicarbonate and water. After drying the ethyl acetate layer with anhydrous sodium sulfate, solvent was removed in vacuo. The residue was refrigerated to produce crystals and hexane was added thereto to obtain the product [21].

Yield: 122.97 g (yield: 00.1%).
TLC: $Rf_5=0.82$.
$[\alpha]_D^{29.5}$: −11.88° (c=1.0, DMF).
m.p.: 45°–47° C.

(22) PF(16–17): Boc-Asn-Ser(Bzl)-OPAC [22]

Methylene chloride (50 ml) was added to the compound [21] (119.9 g, 0.29 M), as was added TFA (250 ml) with ice cooling and the mixture was stirred at room temperature for 1 hour. After the reaction was complete, the reaction mixture was concentrated in vacuo, ether was added thereto and the precipitated crystals were collected by filtration and dried. The crystals were dissolved in dry DMF (400 ml) and the solution was neutralized with NMM to pH 7. HOBt (31.35 g, 0.232 M) and Boc-Asn-OH (53.88 g, 0.232 M) were added thereto, and WSC (42.46 ml, 0.232 M) was added dropwise thereto. The mixture was stirred at room temperature overnight. DMF was removed in vacuo. The residue dissolved in ethyl acetate (500 ml) was washed with 5% aqueous sodium bicarbonate. The precipitated crystals were washed with water and ether to obtain the crystals I (41.79 g) of the product [22]. The ethyl acetate layer of the filtrate was concentrated in vacuo to obtain the residual oily material which was recrystallized from ethyl acetate-ether to obtain the crystals II of the product [22] (6.22 g).

Yield: 48.01 g (yield: 39.2%).
TLC: $Rf_2=0.61$, $Rf_4=0.62$.
m.p.: 174°–176° C.
$[\alpha]_D^{29.5}$: $-5.54°$ (c=1.0, DMF).
Amino acid analysis: Asp 1.22 (1), Ser 1.00 (1).

(23) PF(15–17): Boc-Leu-Asn-Ser(Bzl)-OPAC [23]

Methylene chloride (50 ml) was added to the compound [22] (80.91 g, 0.153 M) and TFA (150 ml) was added with ice cooling thereto. The mixture was stirred at room temperature for 1 hour. The reaction mixture was concentrated in vacuo, ether was added to the residue, whereupon the resulting oily material was separated by decantation and dissolved in dry DMF (150 ml), the solution then being neutralized with NMM to pH 7. HOBt (22.7 g, 0.168 M), Boc-Leu-OH·H₂O (41.9 g, 0.168 M) and DMF (100 ml) were added to the solution, followed by the addition of WSC (30.7 ml, 0.168 M) dropwise at $-15°$ C. The mixture was stirred at room temperature. As the reaction mixture gelled, the mixture was placed in an ice box for 3 days, and water was added thereto. The precipitate was collected by filtration and washed with 5% aqueous sodium bicarbonate and water, then dried to obtain the product [23].

Yield: 88.52 g (yield: 90.3%).
TLC: $Rf_2=0.80$, Rf=0.88.
m.p.: 192°–193° C.
Elementary analysis $[C_{33}H_{44}O_9N_4]$:

|  | C % | H % | N % |
|---|---|---|---|
| Calculated: | 61.86 | 6.92 | 8.75 |
| Found: | 61.81 | 7.05 | 8.56 |

(24) PF(14–17): Boc-His(Tos)-Leu-Asn-Ser(Bzl)-OPAC [24]

Methylene chloride (100 ml) was added to the compound [23] (87.55 g, 0.137 M). TFA (200 ml) was added with ice cooling thereto and the mixture was stirred at room temperature for 70 mins. The reaction mixture was concentrated in vacuo, ether was added to the residue, and the precipitate was filtered, dried, dissolved in dry DMF (200 ml) and the solution was neutralized by adding NMM to pH 7 to obtain a de-Boc compound solution.

Boc-His(Tos)-OH·DCHA (89.2 g, 0.151 M) suspended in ethyl acetate (1 lit.) was washed with 1N H₂SO₄ (500 ml) and the precipitated crystals were filtered. The ethyl acetate layer was washed with water, dried with anhydrous sodium sulfate and the solvent was distilled off in vacuo. The obtained oily materials dissolved in dry DMF (150 ml) and HOBt (20.4 g, 0.151 M) were added to the de-Boc compound solution hereinbefore. WSC (27.6 ml, 0.151 M) was added dropwise thereto at $-15°$ C. and the mixture was stirred at room temperature for 3 days. The solvent was distilled off in vacuo. Water was added to the residue, and the precipitate was filtered and washed with 5% aqueous sodium bicarbonate and water, then dried to obtain the product [24].

Yield: 108.63 g (yield: 85.1%).
TLC: $Rf_2=0.20$, 0.79, $Rf_3=0.55$, 0.87 (partially de-Tos compound was obtained).
m.p.: 154°–156° C.
$[\alpha]_D^{29.5}$: $-18.58°$ (c=1.0, DMF).

(25) PF(13–17): Boc-Lys(Z-Cl)-His-Leu-Asn-Ser(Bzl)-OPAC [25]

Methylene chloride (100 ml) was added to the compound [24] (107.96 g, 0.116 M), followed by the addition of TFA (100 ml) with ice cooling and the mixture was stirred at room temperature for 70 mins. The reaction mixture was concentrated in vacuo, ether was added to the residue, and the precipitate was filtered, dried, dissolved in dry DMF (200 ml) and the resulting solution was neutralized with NMM to pH 7 to obtain a de-Boc solution.

Boc-Lys(Z-Cl)-OH·TBA (62.46 g, 0.128 M) suspended in ethyl acetate (600 ml) was washed with 1N HCl and water. The ethyl acetate layer was dried with anhydrous sodium sulfate and the solvent was distilled off in vacuo. The obtained oily substance and HOBt (17.30 g, 0.128 M) were dissolved in dry DMF (100 ml). This solution was added to the de-Boc solution hereinabove. WSC (24.42 ml, 0.128 M) was added dropwise thereto and the mixture was stirred at room temperature overnight. The solvent was removed in vacuo and the residue was added to 3% aqueous sodium bicarbonate (5 lit.) and the precipitated crystals were washed with water and dried. Ether was added to the methanol solution of the cyrstals to precipitate the crystals and the precipitate was suspended in ethyl acetate and filtered. The same operations were repeated three times to obtain the product [25].

Yield: 114.42 g (yield: 9.18%).
TLC: $Rf_2=0.34$, $Rf_3=0.68$.
m.p.: 200°–202° C.
$[\alpha]_D^{28}$: $-26.94°$ (c—1.0 DMF).

(26) PF(13–17): Boc-Lys(Z-CL)-His-Leu-Asn-Ser(Bzl)-OH [26]

Zinc powder (150 g) was added to the compound [25] (86.9 g, 80 mM) dissolved in acetic acid (500 ml). The mixture was stirred at room temperature for 5 hours and filtered to remove the zinc powder. The reaction filtrate was concentrated in vacuo, ether was added to the residue and the precipitated crystals were filtered to obtain the product [26].

Yield: 84.70 g (yield: 95.2%).
TLC: $Rf_2=0.47$.
m.p.: 240√–250° C.

$[α]_D^{30}$: −19.16° (c=1.0, DMF).

Elementary analysis [$C_{45}H_{52}O_{12}N_9Cl.2CH_3COOH.2H_2O$]:

|  | C % | H % | N % |
|---|---|---|---|
| Calculated: | 53.76 | 6.63 | 11.52 |
| Found: | 52.83 | 6.36 | 11.35 |

Amino acid analysis: Asp 1.01 (1), Ser 0.83 (1), Leu 1 (1), Lys 0.93 (1), His 0.97 (1).

(27) PF(13-34): Boc—Lys(Z—Cl)—His—Leu—Asn— [27]

—Ser(Bzl)—Nle—Glu(OBzl)—

—Arg(Tos)—Val—Glu(OBzl)—Trp—

—Leu—Arg(Tos)—Lys(Z—Cl)—

—Lys(Z—Cl)—Leu—Gln—Asp(OBzl)—

—Val—His—Asn—Tyr(Bzl—Cl_2)—NH_2

Skatole (0.46 g, 3.2 mM), dimethylsulfide (25 ml), ethanedithiol (2.5 ml) and TFA (25 ml) were added to the compound [20] (10.77 g, 3.2 mM). The mixture was stirred at 0° C. for 10 mins. and at room temperature for 60 mins., and the reaction mixture was concentrated in vacuo. Ether was added to the residue, and the precipitate was filtered, dried, and dissolved in dry DMF (100 ml). The resulting solution was neutralized with NMM to pH 7. HOBt (0.51 g, 3.8 mM) and the compound [26] (4.23 g, 3.8 mM) were added to the solution. WSC (0.70 ml) was added at −15° C. and the mixture was stirred at room temperature. DMF was removed in vacuo, water was added to the residue, and the precipitate was filtered, washed with water and dried to obtain the product [27].

Yield: 13.60 g (yield: 100%).

m.p.: 138°-160.5° C. Amino acid analysis: Asp 2.96 (3), Ser 0.62 (1), Glu 3.02 (3) Val 1.72 (2), Leu 3 (3), Tyr 1.06 (1), Lys 3.01 (3), His 1.43 (2), Arg 1.98 (2), Trp 0.60 (1), Nle 1.06 (1).

(28) PF(11-12): Boc-Leu-Gly-OBzl [28]

Dry benzene (50 ml) was added to Boc-Leu-OH.H_2O (4.99 g, 20 mM) dissolved in dry THF (30 ml) and the solvent was azeotropically distilled off. The obtained oily material was dissolved in dry THF (70 ml). H-Gly-OBzl.TosOH (20 mM) and HOBt 2.7 g, 20 mM) were added to the solution, and WSC (5 ml) was added at −5° C., then the mixture was stirred at room temperature overnight. The solvent was distilled off in vacuo and the residue was dissolved in ethyl acetate (100 ml). The solution was washed twice with 1N HCl, twice with 5% aqueous sodium bicarbonate and twice with water. The ethyl acetate layer was dried by adding anhydrous sodium sulfate and concentrated in vacuo to obtain the oily product [28].

(29) PF(10-12): Boc-Asn-Leu-Gly-OBzl [29]

A 4.39N hydrogen chloride/dioxane solution (40 ml) was added to the oily product [28] hereinbefore at −15° C. The mixture was stirred for 90 mins. and concentrated in vacuo. Ether was added to the residue, and the precipitate was collected by filtration, dried and dissolved in dry DMF (30 ml). Et_3N was added at −5° C. to the solution to adjust the pH to 7, and HOBt (0.3 g, 2.2 mM) and Boc-Asn-ONP (7.77 g, 22 mM) were added. This mixture was stirred at room temperature for 3 days. Water was added to the reaction mixture, and the precipitate was extracted with chloroform (200 ml). The chloroform layer was washed with 1N HCl, 5% aqueous sodium bicarbonate and water, dried with anhydrous sodium sulfate, and concentrated in vacuo to remove the solvent. The residue was recrystallized from ethyl acetate-hexane to obtain the product [29].

Yield: 8.0 g (yield: 73.8%).

m.p. 152°-156° C.

$[α]_D^{24}$: −36.1° (c=1.0, DMF).

(30) PF(9-12): Boc-His-Asn-Leu-Gly-OBzl [30]

Methylene chloride (5 ml) was added to the compound [29] (7.36 g, 15.5 mM), TFA (32 ml) was added to the mixture with ice cooling and the mixture was stirred at room temperature for 60 mins. The reaction mixture was concentrated in vacuo, ether was added to the residue, and the precipitate was collected by filtration, dried, and dissolved in dry DMF (40 ml). The resulting solution was neutralized by NMM to pH 7 to obtain a de-Boc solution.

Ethyl acetate (150 ml) and 0.5 N H_2S0_4 (90 ml) were added to Boc-His(Tos)-OH.DCHA (10.99 g, 18.6 mM) and the mixture was shaken. The ethyl acetate layer was washed three times with water, dried with anhydrous sodium sulfate and ethyl acetate was distilled off in vacuo to obtain an oily substance. The oily substance and HOBt (2.5 g, 18.6 mM) were dissolved in dry DMF (60 ml). The solution was added to the de-Boc solution hereinbefore, as was added WSC (3.4 ml, 18.6 mM) at −15° C. The mixture was stirred at room temperature overnight. The solvent was distilled off in vacuo, and the residue was dissolved in ethyl acetate, washed three times with 5% aqueous sodium bicarbonate and twice with water, and dried with anhydrous sodium sulfate whereupon the solvent was distilled off in vacuo. Ether was added to the residue and the precipitated crystals were collected by filtration. In these crystals, the Tos of His was partially removed, and hence in order to completely remove the Tos, the crystals were dissolved in DMF (100 ml), HOBt (7.05 g) was added thereto, and the mixture was stirred at room temperature for 3 days. DMF was removed in vacuo, the residue was dissolved in ethyl acetate, washed twice with 5% aqueous sodium bicarbonate and water, dried with anhydrous sodium sulfate, and then the solvent was distilled off in vacuo. Ether was added to the crystals and the mixture was filtered to obtain the product [30].

Yield: 7.32 g (yield: 74.8%,).

TLC: Rf_2=0.1.

(31) PF(8-12): Boc-Nle-His-Asn-Leu-Gly-OBzl [31]

Methylene chloride (5 ml) was added to the compound [30] (7.32 g, 11.6 mM). TFA (30 ml) was added with ice cooling thereto and the mixture was stirred at room temperature for 40 mins. The reaction mixture was concentrated in vacuo, ether was added to the residue, and the precipitate was filtered, dried and dissolved in dry DMF (40 ml). The solution was adjusted to pH 7 by adding NMM. HOBt (1.9 g, 13.92 mM) and Boc-Nle-OH (3.23 g, 13.92 mM) dissolved in dry DMF were added thereto, as was WSC 2.5 ml, 13.92 mM). The reaction mixture was stirred at room temperature overnight. The solvent was removed in vacuo, water was added to the residue, and the precipitate was filtered, washed twice with 5% aqueous sodium bicarbonate, twice with 1N HCl and three times with water and dried to obtain the product [31].

Yield: 3.70 g (yield: 42.9%).
TLC: $Rf_2=0.20$.

(32) PF(8–12): Boc-Nle-His-Asn-Leu-Gly-OH [32]

10% Pd/C (300 mg) was added to the compound [31] (2.8 g, 3.8 mM) dissolved in ethanol (100 ml) and hydrogen gas was passed therethrough at room temperature for 3 hours. Insoluble materials precipitated in the reaction mixture were filtered and washed with DMF. The filtrate was concentrated in vacuo. Ethanol-ether was added to the residue, and the precipitate was collected by filtration and dried to obtain the product [32].

Yield: 1.76 g (yield: 71.1%).
m.p.: 112.5° C.
TLC: $Rf_2=0.05$.
Amino acid analysis: Asp 0.96 (1), Gly 0.98 (1), Leu 1 (1), His 0.95 (1), Nle 0.94 (1).

(33) PF(8–34):

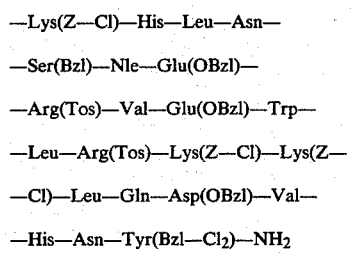

Boc—Nle—His—Asn—Leu—Gly— [33]
—Lys(Z—Cl)—His—Leu—Asn—
—Ser(Bzl)—Nle—Glu(OBzl)—
—Arg(Tos)—Val—Glu(OBzl)—Trp—
—Leu—Arg(Tos)—Lys(Z—Cl)—Lys(Z—
—Cl)—Leu—Gln—Asp(OBzl)—Val—
—His—Asn—Tyr(Bzl—Cl$_2$)—NH$_2$

Skatole (0.33 g, 2.5 mM), dimethylsulfide (25 ml), ethanedithiole (2.5 ml) and TFA (25 ml) were added to the compound (10.60 g, 2.5 mM). The mixture was stirred at 0° C. for 10 mins. and at room temperature for 50 mins., and concentrated in vacuo. Ether was added to the residue, and the precipitate was filtered, dried, dissolved in DMF (100 ml). NMM was added with ice cooling to adjust the pH to 7. HOBt (0.36 g, 2.7 mM) and the compound [32](1.76 g, 2.7 mM) were added to the solution, and WSC (0.5 ml) was added at −15° C. thereto. The mixture was stirred at room temperature overnight. The precipitate was filtered, washed with water, dried and reprecipitated from ethanol-ether to obtain the product [33].

Yield: 10.94 g (yield: 91.7%).
m.p.: 140.5°–162° C.
$[\alpha]_D^{28}$: −1.94° (c=0.52, DMF).
Amino acid analysis: Asp 3.87 (4), Ser 0.76 (1), Glu 3.34 (3), Gly 0.77 (1), Val 1.84 (2), Leu 4 (4), Tyr 1.04 (1), Lys 3.28 (3), His 2.37 (3), Arg 2.14 (2), Trp 0.73 (1), Nle 2.07 (2).

(34) PF(7): Boc-Leu-OPAC [34]

Et$_3$N (12.5 ml, 90 mM) was added dropwise to Boc-Leu-OH. H$_2$O (15.0 g, 60 mM) and phenacyl bromide (17.9 g, 90 mM) dissolved in DMF (100 ml). The mixture was stirred at 30° C. for 2 hours. Potassium acetate (4.42 g, 45 mM) was added thereto, and the mixture was stirred at room temperature for 45 mins. and DMF was distilled off. The residue dissolved in ethyl acetate was washed twice with 5% aqueous sodium bicarbonate and twice with water. The ethyl acetate layer was dried with anhydrous sodium sulfate and the solvent was distilled off in vacuo. The residue was placed in an ice box and the precipitated crystals were dried to obtain the product [34].

Yield: 21.23 g (yield: 100%).
TLC: $Rf_1=0.89$.

(35) PF(6–7): Boc-Gln-Leu-OPAC [35]

Methylene chloride (20 ml) was added to the compound [34] (20.96 g, 60 mM); TFA (80 ml) was added thereto with ice cooling, and the mixture was stirred at room temperature for 40 mins., and concentrated in vacuo. Ether was added to the residue, and the precipitate was filtered, dried, dissolved in dry DMF (70 ml), and the resulting solution was adjusted to pH 7 by adding NMM with ice cooling. HOBt (8.1 g, 60 mM) and Boc-Gln-OH (14.78 g, 60 mM) dissolved in dry DMF (90 ml) were added to the solution, as was added WSC (10.9 ml, 60 mM) at −15° C. and the mixture was stirred at room temperature overnight. DMF was removed in vacuo, and the residue was dissolved in ethyl acetate and washed twice with 5% aqueous sodium bicarbonate, twice with 1N HCl and three times with water. The ethyl acetate layer was dried with anhydrous sodium sulfate, the solvent was distilled off in vacuo, and hexane was added to the precipitated crystals, which were filtered and dried to obtain the product [35].

Yield: 17.25 g (yield: 60.2%).
TLC: $Rf_1=0.38$.

(36) PF(5–7): Boc-Ile-Gln-Leu-OPAC [36]

Methylene chloride (10 ml) was added to the compound [35] (17.19 g, 36 mM), TFA (70 ml) was added thereto with ice cooling. The mixture was stirred at room temperature for 60 mins., and concentrated in vacuo. The residue was dried in vacuo, dissolved in dry DMF (130 ml) and the solution was adjusted to pH 7 with ice cooling by adding NMM. HOBt (5.3 g, 39.6 mM) and Boc-Ile-OH.½ H$_2$O (9.5 g, 39.6 mM) were added dropwise to the solution and the solution was stirred at room temperature overnight. DMF was distilled off in vacuo, 5% aqueous sodium bicarbonate was added to the residue, and the precipitate was filtered, washed once with 5% aqueous sodium bicarbonate, twice with 1N HCl and three times with water and dried. The precipitate was resedimented from ethanol-ether to obtain the product [36].

Yield: 16.35 g (yield: 76.9%).
TLC: $Rf_1=0.41$, $Rf_2=0.68$.

(37) PF(4–7): Boc-Glu(OBzl)-Ile-Gln-Leu-OPAC [37]

Methylene chloride (10 ml) was added to the compound [36] (16.24 g, 27.5 mM). TFA (70 ml) was added to the solution, stirred at room temperature for 60 mins. and the reaction mixture was concentrated in vacuo. Ether was added to the residue, and the precipitate was filtered, dried, and dissolved in DMF (100 ml). The resulting solution was adjusted to pH 7 by adding NMM with ice cooling. HOBt (4.09 g, 30.25 mM) and Boc-Glu(OBzl)-OH (10.2 g, 30.25 mM) dissolved in dry DMF (50 ml) were added to the solution, as was added WSC (5.5 ml) dropwise at −15° C. and the mixture was stirred at room temperature overnight. DMF was distilled off in vacuo and 5% aqueous sodium bicarbonate was added to the residue. The precipitate formed was filtered, washed once with 5% aqueous sodium bicarbonate, twice with 1N HCl and four times with water and dried. The product [37] was obtained by reprecipitation from ethanol-ether.

Yield: 21.68 g (yield: 97.1%).

TLC: $Rf_1=0.52$.

(38) PF(3-7):
Boc-Ser(Bzl)-Glu(OBzl)-Ile-Gln-Leu-OPAC [38]

Methylene chloride (10 ml) was added to the compound [37] (21.46 g, 26.5 mM), as was added TFA (90 ml) with ice cooling. The mixture was stirred at room temperature, and concentrated in vacuo. Ether was added to the residue, and the precipitate was filtered, dried, and dissolved in dry DMF (150 ml). The solution was adjusted to pH 7 by adding NMM with ice cooling. HOBt (3.9 g, 29.15 mM) and Boc-Ser(Bzl)-OH (8.6 g, 29.15 mM) dissolved in dry DMF (50 ml) were added to the solution. WSC (5.3 ml, 29.15 mM) was added thereto and the mixture was stirred at room temperature overnight. DMF was distilled off in vacuo, 5% aqueous sodium bicarbonate was added to the residue, and the precipitate was filtered. The precipitate was washed once with 5% aqueous sodium bicarbonate, twice with 1N HCl and four times with water, suspended in ether and filtered to obtain the product [38].

Yield: 24.8 g (yield: 94.7%).
TLC: $Rf_1=0.53$.

(39) PF(2-7):
Boc-Val-Ser(Bzl)-Glu(OBzl)-Ile-Gln-Leu-OPAC [39]

Methylene chloride (20 ml) was added to the compound [38] (24.68 g, 25 mM), as was added TFA (100 ml) with ice cooling and the mixture was stirred at room temperature for 50 mins. The reaction mixture was concentrated in vacuo, ether was added to the residue, and the precipitate was filtered and dried. The dried precipitate was dissolved in dry DMF (120 ml) and the solution was adjusted to pH 7 by adding NMM with ice cooling. HOBt (4.05 g, 30 mM) and Boc-Val-OH (6.5 g, 30 mM) dissolved in dry DMF (80 ml) were added to the solution, as was added WSC (5.5 ml, 30 mM) dropwise at $-15°$ C., and the mixture was stirred at room temperature overnight. The precipitate formed was filtered after adding water, and washed twice with 5% aqueous sodium bicarbonate, twice with 1N HCl and four times with water, suspended in ether and filtered to obtain the product [39].

Yield: 26.32 g (yield: 96.8%).
TLC: $Rf_1=0.49$.

(40) PF(1-7):
Boc-Ser(Bzl)-Val-Ser(Bzl)-Glu(OBzl)-Ile-Gln-Leu-OPAC [40]

Methylene chloride (20 ml) was added to the compound [39] (26.07 g, 24 mM). TFA (100 ml) was added thereto and the mixture was stirred at room temperature for 40 mins. The reaction mixture was concentrated in vacuo, ether was added to the residue, and the precipitate was filtered, dried and dissolved in dry DMF (100 ml). The solution was adjusted to pH 7 by adding NMM. HOBt (3.9 g, 28.8 mM) and Boc-Ser(Bzl)-OH (8.5 g, 28.8 mM) is dissolved in dry DMF (50 ml) were added to the solution, as was added WSC (5.3 ml, 28.8 mM) at $-15°$ C. and the mixture was stirred at room temperature overnight. A precipitate was formed in the reaction mixture and water was added thereto. The precipitate was filtered, washed with 5% aqueous sodium bicarbonate, 1N HCl and water, suspended in ether and filtered. The same operation was repeated twice to obtain the product [40].

Yield: 28.0 g (yield: 92.3%).
TLC: $Rf_1=0.53$.

(41) PF(1-7):
Boc-Ser(Bzl)-Val-Ser(Bzl)-Glu(OBzl)-Ile-Gln-Leu-OH [41]

Zinc powder (15 g) was added to the compound [40] (12.6 g, 10 mM) dissolved in acetic acid (300 ml) and the mixture was stirred at 50° C. for 4 hours, then zinc powder was filtered off. Acetic acid was distilled off in vacuo, ether was added to the residue, and the precipitated crystals were collected and washed to obtain the product [41].

Yield: 11.15 g (yield: 97.4%).
m.p.: 260° C. (decomp.).
TLC: $Rf_1=0.14$, $Rf_2=0.64$.
Amino acid analysis: Ser 1.81 (2), Glu 2.02 (2), Val 0.95 (1), Leu 1 (1), Ile 0.92 (1).

(42) Protected - [Nle$^8$, Nle$^{18}$, Tyr$^{34}$]-h-PTH(1-34)NH$_2$:

Boc—Ser(Bzl)—Val—Ser(Bzl)— [42]

—Glu(OBzl)—Ile—Gln—Leu—Nle—His—

—Asn—Leu—Gly—Lys(Z—Cl)—His—Leu—

—Asn—Ser(Bzl)—Nle—Glu(OBzl)—

—Arg(Tos)—Val—Glu(OBzl)—Trp—Leu—

—Arg(Tos)—Lys(Z—Cl)—Lys(Z—Cl)—

—Leu—Gln—Asp(OBzl)—Val—His—Asn—

—Tyr(Bzl—Cl$_2$)—NH$_2$

Skatole (0.30 g, 2.28 mM), dimethylsulfide (25 ml), ethanedithiol (2.5 ml) and TFA (25 ml) were added to the compound [33] (10.86 g, 2.28 mM) with ice cooling. The mixture was stirred at room temperature for 60 mins. and concentrated in vacuo. Ether was added to the residue, and the precipitate was dried and dissolved in a mixture of dry DMF (100 ml) and DMSO (10 ml). The solution was adjusted to pH 7 by adding NMM with ice cooling. HOBt (0.37 g, 2.74 mM) and the compound [41] (3.14 g, 2.74 mM) were added thereto, as was added WSC (0.50 ml, 2.74 mM) at $-15°$ C. and the mixture was stirred at room temperature overnight. Water was added to the reaction mixture, and the precipitate was filtered and washed with water and ethanol-ether to obtain the product [42].

Yield: 12.87 g (yield: 97.3%).
m.p.: 139.5°–175° C.
$[\alpha]_D^{28}$: $-1.97°$ (c=0.51, DMF).
Amino acid analysis: Asp 3.72 (4), Ser 2.76 (3), Glu 5.58 (5), Gly 0.69 (1), Val 2.86 (3), Ile 1.11 (1), Leu 5 (5), Tyr 0.99 (1), Lys 2.87 (3), His 2.19 (3), Arg 2.06 (2), Trp 0.65 (1), Nle 1.96 (2).

(43) [Nle$^8$, Nle$^{18}$, Tyr$^{34}$]-h-PTH(1-34)NH$_2$

Anisole (3.5 ml), ethandithiol (0.35 ml), dimethylsulfide (3.5 ml) and anhydrous HF (35 ml) were added to the compound [42] (2.9 g, 0.5 mM) and the mixture was stirred for 60 mins. HF was distilled off in vacuo, ether was added to the residue, and the precipitate was collected and dissolved in 0.1 N acetic acid. The solution was passed through a column (3.5×12 cm of Dowex X1 (acetate type, trade name) and the ninhydrin positive fractions were collected and freeze-dried to obtain the crude product (1.87 g). The product dissolved in 0.1 N acetic acid (50 ml) was charged on a column (2×33 cm)

of CM-cellulose and eluted by linear gradient elution of 0.05 M ammonium acetate (pH 5.1, 1 lit.) - 0.4 M ammonium acetate (pH 6.0, 1 lit.) Each 9.0 ml fraction showing approximately $Rf_6=0.30$, the fractions Nos. 74-84, was collected and freeze-dried. The freeze-dried material was dissolved in a small amount of 0.1 N HCl, and the solution was charged on a column ($3\times115$ cm) of Sephadex G-25 and eluted with 0.1 N acetic acid. Each fraction was checked at an absorbance of 280 nm and the fractions showing one major peak were collected and freeze-dried to obtain [$Nle^8$, $Nle^{18}$, $Tyr^{34}$]-h-PTH(1-34)$NH_2$.

Yield: 140 mg.

TLC: $Rf_6=0.30$.

Amino acid analysis (hydrolyzed by 6N HCl containing 3% thioglycolic acid): Asp 3.98 (4), Ser 2.10 (3), Glu 4.93 (5), Gly 0.97 (1), Val 2.66 (3), Ile 0.87 (1), Leu 5.00 (5), Tyr 1.11 (1), Lys 3.26 (3), His 2.30 (2), Arg 2.03 (2), Trp 0.62 (1), Nle 2.22 (2).

HPLC: column; nucleosil 5C18 (4 mmID$\times$150 mm).

Buffer: 0.1% acetic acid-acetonitrile containing 0.1 M phosphate (ratio of acetonitrile is determined by linear gradient of 20% for initial 5 mins. and 20-40% for subsequent 20 mins.)

Flow rate: 1 ml/min.

Detection: 225 nm.

Result: single peak at 19.07 min.

EXAMPLE 2

[$Nle^8$, $Nle^{18}$, $Phe^{34}$]-h-PTH(1-34)$NH_2$:

(44) PF(23-34):

Boc-Trp-Leu-Arg(Tos)-Lys(Z-Cl)-Lys(Z-Cl)-Leu-Gln-Asp(OBzl)-Val-His-Asn-Phe-$NH_2$ [43]

Z(OMe)-Gln-Asp(OBzl)-Val-His-Asn-Phe-$NH_2$ prepared according to the method of Jap. Pat. Unexam. Publ. No. 55-113753 (1.68 g) was suspended in a small amount of methylene chloride. TFA (7 ml) was added thereto with ice cooling and the mixture was stirred at room temperature for 30 mins. TFA was distilled off in vacuo, ether was added to the residue, and the precipitated crystals were filtered and dried. The crystals dissolved in dry DMF (30 ml) were neutralized with a small amount of NMM. The compound [12] obtained in Example 1 (2.43 g), HOBt (0.22 g) and dry DMF (20 ml), and WSC (0.3 ml, 1.1 molar equivalent) at $-15°$ C. were mixed and stirred at room temperature overnight. DMF was distilled off in vacuo. The residue was washed once with 5% aqueous sodium bicarbonate and twice with water, suspended in methanol, ether was added thereto, and the residue was filtered and dried to obtain the product [43].

Yield: 3.62 g.

m.p 262°-271° C.

$[\alpha]_D^{25}$: -4.51 (c=0.3, DMF).

Amino acid analysis: Asp 1.94 (2), Glu 0.96 (1), Val 0.71 (1), Leu 2.00 (2), Phe 0.98 (1), Lys 2.09 (2), His 0.58 (1), Arg 0.91 (1), Trp 0.78 (1).

[44]

(45) PF(18-34): Boc—Nle—Glu(OBzl)—Arg(Tos)—Val—

—Glu(OBzl)—Trp—Leu—Arg(Tos)—

—Lys(Z—Cl)—Lys(Z—Cl)—Leu—Gln—

—Asp(OBzl)—Val—His—Asn—Phe—$NH_2$

Skatole (0.5 g, 3.5 mM), dimethylsulfide (25 ml), ethandithiol (2.5 ml) and TFA (25 ml) were added to the compound [13] prepared in Example 1 (8.9 g, 3.5 mM) and the mixture was stirred at 0° C. for 10 mins. and at room temperature for 45 mins. and concentrated in vacuo. Ether was added to the residue, and the precipitate was filtered, dried, and dissolved in DMF (100 ml). The solution was neutralized with NMM. HOBt (0.54 g) and the compound [43] (4.3 g) were added thereto, as was added WSC (0.73 ml) at $-15°$ C. and the mixture was stirred at room temperature for 2 days. DMF was distilled off in vacuo. 5% aqueous sodium bicarbonate was added to the residue, and the precipitate was filtered and washed with water. The product was dissolved in ethanol and ether was added to induce precipitation. The same operation was repeated twice to obtain the product [44].

Yield: 11.12 g (yield: 95.6%).

TLC: $Rf_2=0.73$.

m.p.: 252° C. (decomp.).

$[\alpha]_D^{28}$: -4.8 (c=0.53, DMF).

Amino acid analysis: Asp 1.98 (2), Glu 3.04 (3), Val 1.69 (2), Leu 2 (2), Phe 1.07 (1), Lys 1.93 (2), His 0.59 (1), Arg 1.97 (2), Trp 0.35 (1), Nle 1.07 (1).

[45]

(46) PF(13-34): Boc—Lys(Z—Cl)—His—Leu—Asn—

—Ser(Bzl)—Nle—Glu(Obzl)—

—Arg(Tos)—Val—Glu(OBzl)—Trp—

—Leu—Arg(Tos)—Lys(Z—Cl)—

—Lys(Z—Cl)—Leu—Gln—Asp(OBzl)—

—Val—His—Asn—Phe—$NH_2$

Skatole (0.46 g), dimethylsulfide (25 ml), ethandithiol (2.5 ml) and TFA (25 ml) were added to the compound [20] prepared in Example 1 (10.77 g). The mixture was stirred at 0° C. for 10 mins. and at room temperature for 60 mins. and concentrated in vacuo. Ether was added to the residue, and the precipitate was filtered and dried. The dried material was dissolved in dry DMF (100 ml) and the solution was neutralized to pH 7 by adding NMM. HOBt (0.51 g) and the compound [44] (4.23 g) were added thereto, as was added WSC (0.70 ml) at $-15°$ C. and the mixture was stirred at room temperature. DMF was distilled off in vacuo, water was added thereto, and the precipitate was filtered, washed with water and dried to obtain the product [45].

Yield: 13.60 g.

m.p.: 140°-155° C.

$[\alpha]_D^{28}$: -2.00 (c=0.56, DMF).

Amino acid analysis: Asp 2.96 (3), Ser 0.62 (1), Glu 3.02 (3), Val 1.72 (2), Leu 3 (3), Phe 1.06 (1), Lys 3.01 (3), His 1.43 (2), Arg 1.98 (2), Trp 0.60 (1), Nle 1.06 (1).

[46]

(47) PF(8-34): Boc—Nle—His—Asn—Leu—Gly—

—Lys(Z—Cl)—His—Leu—Asn—

—Ser(Bzl)—Nle—Glu(OBzl)—

—Arg(Tos)—Val—Glu(OBzl)—Trp—

—Leu—Arg(Tos)—Lys(Z—Cl)—

-continued

—Lys(Z—Cl)—Leu—Gln—Asp(OBzl)—

—Val—His—Asn—Phe—NH$_2$

Skatole (0.33 g), dimethylsulfide (25 ml), ethandithiol (2.5 ml) and TFA (25 ml) were added to the compound [45] (10.60 g). The mixture was stirred at 0° C. for 10 mins. and at room temperature for 50 mins., and concentrated in vacuo. Ether was added to the residue, and the precipitate was filtered, dried, and dissolved in dry DMF (100 ml). The solution was adjusted to pH 7 by adding NMM with ice cooling. HOBt (0.36 g, 2.7 mM) and the compound [32] (1.76 g, 2.7 mM) in Example 1 were added to the solution, as was added WSC (0.5 ml) at −15° C. and the mixture was stirred at room temperature overnight. The precipitated material was filtered, washed with water, dried and reprecipitated from ethanol-ether to obtain the product [46].

Yield: 10.94 g.
m.p.: 143°–161° C.
$[\alpha]_D^{28}$: −2.01 (c=0.52, DMF).
Amino acid analysis: Asp 3.87 (4), Ser 0.76 (1), Glu 3.34 (3), Gly 0.77 (1), Val 1.84 (2), Leu 4 (4), Phe 1.04 (1), Lys 3.28 (3), His 2.37 (4), Arg 2.14 (2), Trp 0.73 (1), Nle 2.07 (2).

(48) Protected - [Nle$^8$, Nle$^{18}$]-h-PTH(1-34)NH$_2$:

Boc—Ser(Bzl)—Val—Ser(Bzl)— [47]

—Glu(OBzl)—Ile—Gln—Leu—Nle—His—

—Asn—Leu—Gly—Lys(Z—Cl)—His—Leu—

—Asn—Ser(Bzl)—Nle—Glu(OBzyl)—

—Arg(Tos)—Val—Glu(OBzl)—Trp—Leu—

—Arg(Tos)—Lys(Z—Cl)—Lys(z—Cl)—

—Leu—Gln—Asp(OBzl)—Val—His—

—Asn—Phe—NH$_2$

Skatole (0.30 g), dimethylsulfide (25 ml), ethandithiol (2.5 ml) and TFA (25 ml) were added to the compound [46] (10.86 g). The mixture was stirred at room temperature for 60 mins. with ice cooling and concentrated in vacuo. Ether was added to the residue, and the precipitate was filtered and dried. The dried material was dissolved in a mixture of dry DMF (100 ml) and DMSO (10 ml) and the resulting solution was adjusted to pH 7 by adding NMM with ice cooling. HOBt (0.37 g) and the compound [41] in Example 1 (3.14 g) were added thereto, and WSC (0.51 ml) was added at −15° C., then the mixture was stirred at room temperature overnight. Water was added to the reaction mixture, and the precipitate was filtered, washed with water, then washed with ethanol-ether to obtain the product [47].

Yield: 12.87 g.

m.p.: 141°–171° C.
$[\alpha]_D^{28}$ −1.97° (c=0.71, DMF).
Amino acid analysis: Asp 3.72 (4), Ser 2.76 (3), Glu 5.58 (5), Gly 0.69 (1), Val 2.86 (3), Ile 1.11 (1), Leu 5 (5), Phe 1.01 (1), Lys 2.87 (3), His 2.19 (3), Arg 2.06 (2), Trp 0.65 (1), Nle 1.96 (2).

(49) [Nle$^8$, Nle$^{18}$]-h-PTH(1-34)NH$_2$

Anisole (3.5 ml), ethandithiol (0.35 ml), dimethylsulfide (3.5 ml) and anhydrous HF (35 ml) were added to the compound [47] (2.9 g) at 0° C. and the mixture was stirred for 60 mins. HF was distilled off in vacuo. Ether was added to the residue, and the precipitate was collected and dissolved in 0.1N acetic acid. The solution was passed through a column (3.5×12 cm) of Dowex Xl (acetate type), and the ninhydrin positive fractions were collected and freeze-dried to obtain the crude product (1.87 g). This was dissolved in 0.1 N acetic acid (50 ml) and charged on a column (2×33 cm) of CM-cellulose, then eluted with a linear gradient ammonium acetate (pH 5.1, 1 lit.) to 0.04 M ammonium acetate (pH 6.0, 1 lit.) Each 9.0 ml fraction was fractionated, and fractions No. 74–84 showing approximately Rf$_8$=0.28 were collected and freeze-dried. The freeze-dried powder was dissolved in a small amount of 0.1 N HCl and charged on a column (3×115 cm) of Sephadex G-25 and eluted with 0.1 N acetic acid. Fractions showing absorbance at 280 nm in a major peak were collected and freeze-dried to obtain [Nle$^8$, Nle$^{18}$]-h-PTH(1-34)NH$_2$.

Yield: 140 mg.
TLC: Rf$_8$=0.28.
Amino acid analysis (hydrolyzed by 6N HCl containing 3% thioglycolic acid): Asp 3.98 (4), Ser 2.10 (3), Glu 4.93 (5), Gly 0.97 (1), Val 2.66 (3), Ile 0.87 (1), Leu 5.00 (5), Phe 1.01 (1), Gly 3.26 (3), His 2.30 (3), Arg 2.03 (2), Trp 0.62 (1), Nle 2.22 (2).
HPLC: column; nucleosil 5C18 (4 mmID×150 mm).
Buffer: 0.1% acetic acid-acetonitrile containing 0.1 M phosphate (ratio of acetonitrile; initial 5 mins. 20%, later 20 mins. 20–40% linear gradient).
Flow rate: 1 ml/min.
Detection: 225 nm.
Result: single peak at 18.96 min.
What is claimed is:

1. A peptide of the formula

H—Ser—Val—Ser—Glu—Ile—Gln—Leu—Nle—His—Asn—

Leu—Gly—Lys—His—Leu—Asn—Ser—Nle—Glu—Arg—Val—

Glu—Trp—Leu—Arg—Lys—Lys—Leu—Gln—Asp—Val—His—

Asn—A—NH$_2$ wherein A is Tyr or Phe, or a pharmaceutically acceptable salt thereof.

2. An iodine-125 labelled [Nle$^8$, Nle$^{18}$, Tyr$^{34}$]-h-PTH((1-34)NH$_2$.

* * * * *